(12) United States Patent
Kupczunas et al.

(10) Patent No.: US 12,066,395 B2
(45) Date of Patent: Aug. 20, 2024

(54) SENSOR FOR THE IMPEDANCE MEASUREMENTS OF THE BIOLOGICAL OR CHEMICAL FACTOR SAMPLE AND THE METHOD FOR THE DETECTION OF THE BIOLOGICAL OR CHEMICAL FACTOR IN THE SAMPLE USING SUCH A SENSOR

(71) Applicant: Sensdx S.A., Warsaw (PL)

(72) Inventors: Artur Kupczunas, Kalisz (PL); Dawid Nidzworski, Gdansk (PL); Krzysztof Urbanski, Bielawa (PL); Jakub Mnich, Wroclaw (PL); Katarzyna Pala, Wroclaw (PL); Tomasz Gondek, Katna (PL); Elzbieta Czaczyk, Pruszcz Gdanski (PL); Karolina Dziabowska, Elblag (PL)

( * ) Notice: Subject to any disclaimer, the term of this patent is extended or adjusted under 35 U.S.C. 154(b) by 959 days.

(21) Appl. No.: 16/968,203

(22) PCT Filed: Feb. 6, 2019

(86) PCT No.: PCT/IB2019/050935
§ 371 (c)(1),
(2) Date: Aug. 7, 2020

(87) PCT Pub. No.: WO2019/155366
PCT Pub. Date: Aug. 15, 2019

(65) Prior Publication Data
US 2021/0025876 A1    Jan. 28, 2021

(30) Foreign Application Priority Data
Feb. 7, 2018 (PL) .......................... 424524

(51) Int. Cl.
*G01N 27/327* (2006.01)
*G01N 27/447* (2006.01)
*G01N 33/543* (2006.01)

(52) U.S. Cl.
CPC ....... *G01N 27/327* (2013.01); *G01N 27/4473* (2013.01); *G01N 33/5438* (2013.01)

(58) Field of Classification Search
None
See application file for complete search history.

(56) References Cited

U.S. PATENT DOCUMENTS

2005/0252777 A1* 11/2005 Li ..................... G01N 27/3276
                                                                  204/600

FOREIGN PATENT DOCUMENTS

WO    WO-2004113915 A1 * 12/2004 ....... G01N 33/48771

OTHER PUBLICATIONS

T. Matsubara, et al., "Highly sensitive detection of influenza virus by boron-doped diamond electrode terminated with sialic acid-mimic peptide", Proceedings of the National Academy of Science, 113(32): p. 8981-8984, Aug. (Year: 2016).*

* cited by examiner

*Primary Examiner* — J. Christopher Ball
(74) *Attorney, Agent, or Firm* — BelayIP

(57) ABSTRACT

The subject of the present invention is the sensor for the impedance measurements of the biological or chemical factor sample in the potentiostat system comprising the reference electrode RE and counting electrode CE with the electric contacts leading to the edge of the sensor in the form of the edge connector characterised in that it contains n working electrodes WEn, wherein n>2 and preferably n is in the range 2 to 256, and the reference electrode RE is common for all working electrodes WEn and the fragment thereof present by the working electrode WEn forms the measuring segment RE-CE-WEn. The subject of the invention is also the detection method of the chemical or biological factor in the sample using such a sensor.

13 Claims, 9 Drawing Sheets

SENSOR FOR THE IMPEDANCE MEASUREMENTS OF THE BIOLOGICAL OR CHEMICAL FACTOR SAMPLE AND THE METHOD FOR THE DETECTION OF THE BIOLOGICAL OR CHEMICAL FACTOR IN THE SAMPLE USING SUCH A SENSOR

CROSS REFERENCE TO RELATED APPLICATIONS

This application is a national phase of International Application No.: PCT/IB2019/050935 A2, filed on 6 Feb. 2019, which claims priority to Polish Patent Application P.424524 filed on 7 Feb. 2018. The contents of the above-references applications are expressly incorporated herein by reference to their entireties.

FIELD OF THE INVENTION

The subject of the invention is the sensor for the impedance measurements of the biological or chemical factor sample in the potentiostat system comprising the reference electrode (RE) and counting electrode (CE) with the electric contacts leading to the edge of the sensor in the form of the edge connector.

BACKGROUND

In the state of the art there is a number of inventions which solve the problem of the sensitive measurements of the agents in the biological samples. The US2014273549A1 application presents the solution which relates to the multi-electrode single-channel biometric sensor (e.g. for the measurement of the glucose in blood) in the form of a strip connected with the measuring device using a slot. The strip contains many fields made of a conductor and the rim of the strip is formed in such a manner to fit the sensor slot and is equipped with many contacts. The described device contains one measurement segment consisting of a few electrode. The WO2013114291A1 application relates to the multichannel temperature sensor in form of a plate with the formed tracks leading to the edge connector for connection with the slot of the sensing device. The plate contains many fields made of a conductor and the rim is formed to fit the sensor slot and the plate is equipped with many contact fields (edge connectors). The measurements are conducted simultaneously and in parallel. In the described solution each measuring field is an independent measuring system, and multi-channel character is achieved by the multiplication of measuring systems; the number of the circuit lines is also multiplicated. Each of these measuring systems operates independently, thus the sample measurement is not conducted in the same conditions in each channel. Additionally, such a distribution of electrodes increase the measurement time and does not give the possibility to eliminate the measurement errors.

U.S. Pat. No. 6,391,558B1 patent presents the system for detection of the nucleic acids based on the electrochemical method. The system utilises the electrode on the PCB surface including the array of working and reference electrodes. The electric potential applied to the working electrode is multiplexed, what enables the detection of various ligands in one sample. The sensor electrode is connected with the analyser which detects the electric pulses and signal changes caused by the interactions on the electrode.

The patent application US20030042150A1 describes the electrochemical sensor for the detection of the blood parameters, such as glucose concentration, cholesterol level, and other. The system consists of many electrodes enabling the simultaneous measurement of multiple parameters.

On the other hand, U.S. Pat. No. 6,391,558B1 patent describes the nucleic acid detection method using the electrodes on the printed plates. The electrode can be made of carbon or metals, including copper, nickel, gold, platinum, palladium, and other. The printed plates are manufactured using screen printing and are subsequently subjected to the photolithography. The description does not cover the possibility to perform the simultaneous measurements on number of electrodes without multiplexing.

The biosensors based on the electrochemical measurements are often used in the Point-of-Care (PoC) devices. Ward et al. in publication PLOS ONE 2014 9 3 e91732. "Detecting *P. aeruginosa* with a Novel Biosensor" described the method for the determination of *Pseudomonas aeruginosa* using Electrochemical Impedance Spectroscopy (EIS). The measurement and results analysis are based on the change in the impedance after connection of the microorganisms via pili, flagella, or extracellular proteins with the biofilm on the electrode surface what causes the transfer of charge, or by the detection of the metabolites produced by the microorganisms.

The international patent application WO2001083674A1 describes the method for detection of the reagents using the electrochemical biosensor made of the electrodes covered with the monolayer of the biological molecules, preferably the biotin selectively interacting with the streptavidin. On the other hand, Moreira et al. (Sensors and Actuators B 223 (2016) 927-935) describe the utilisation of the screen print technology to manufacture the sensors based on the silver electrodes. The sensor included artificial antibodies recognising cancer biomarkers. The antibodies detection signal was measured using various methods such as cyclic voltammetry (CV), electrochemical impedance spectroscopy (ESI), squarewave voltammetry (SWV).

The drawback of the inventions described in the state of the art is the lack of possibility to conduct parallel multichannel measurement for all measurements segments, what negatively influences the measurement speed and its accuracy. To conduct the multichannel measurements using the solutions described in the state of the art, one sensor system with the signal multiplexation is used, where in a given while only one measurement segment is powered and registered, and subsequently the system switches the power and measurement to the next measurement segment. Finally, there is no possibility to perform the simultaneous measurement. Each measurement segment has its separate set of electrodes, the generated measurement errors, constant and random, detected on the reference electrodes cannot be compensated in any way because each reference electrode is a separate electric circuit (constant error of each electrode) and the random errors are impossible to define due to measurements of segments in various time.

Unexpectedly, it turned out that the presented invention solves this problem.

SUMMARY OF THE INVENTION

The subject of the present invention is the sensor for the impedance measurements of the biological or chemical factor sample in the potentiostat system comprising the reference electrode RE and the counting electrode CE with the electric contacts leading to the edge of the sensor in the form of the edge connector which preferably comprises n working electrodes WEn, wherein n>2 and preferably n is in the range 2 to 256, and the reference electrode RE is common for all working electrodes WEn and the fragment thereof present by the working electrode WEn forms the measuring segment RE-CE-WEn.

Preferably, at least two, and more preferably all WEn electrodes are covered on the outer surface with the layer of the sensory material the material which reacts only with one type of the biological or chemical factor in the sample.

Preferably, at least two WEn electrodes are covered with different sensory materials.

Preferably, the sensory material is the material of a biological or synthetic type, and especially these are antibodies, antibody fragments, peptides, nucleic acid sequences for the detection of the biological or chemical factor in the sample.

Preferably, the working electrodes WEn have the shape of the uniform circles and are located symmetrically to the counting electrode CE, wherein the edges of the counting electrode CE have the shape of the sections of the circumferences which are concentric with these circles, wherein the reference electrode RE is located between the counting electrode CE and the working electrodes WEn and the shape of the reference electrode RE is the same as the contour of the counting electrode CE.

Preferably, comprises the additional connecting and/or non-connecting electrodes to code the number of the working electrode WEn, where n>2 and preferably n is in the range of 2 to 256.

Preferably, the arrangement of the working electrodes WEn, the counting electrode CE, and the reference electrode RE constitute a repeating measurement segments of identical shape and distances in each measurement segments between the working electrode WEn, the counting electrode CE, and the reference electrode RE are the same, and in addition the area of working electrode WEn, the counting electrode CE fragment, and the reference electrode RE fragment are respectively the same in each segment. The shape of the reference electrode RE includes distribution of the electric field gradient in the polarised sensor reflecting essentially identical potential value in a polarised electrolyte.

Preferably, the arrangement and shape of the working electrodes WEn, the reference electrode RE, and the counting electrode CE has its symmetry axis.

Preferably, the edge connector has the contact fields which constitutes an electric circuit independent of the WEn, RE and CE electrodes intended for the identification of the correct location of sensor in the slot of the measurement system by connecting the measurement slot contacts during insertion of the sensor into the slot.

Preferably, it contains 9 contact spots used to code the sensor number.

Preferably, the edge connector is the HDMI plug (High Definition Multimedia Interface) or the DisplayPort plug (universal digital interface).

The subject of the present invention is the detection method of the biological or chemical factor in the sample characterised in that the sample of the biological or chemical factor in the form of the electrolyte or solution is placed in the device according to any of the preceding claims 1 to 11 that all the working electrodes WEn, counting electrode CE, and the reference electrode RE are covered with the mentioned sample in the form of solution, and subsequently 2 to 256 sample measurements are conducted simultaneously, especially using the impedance spectroscopy technique or the voltammetry and based on the results of these measurements the presence of the biological or chemical factor in the sample is determined.

Preferably, the measurement is conducted in the reverse configuration where the reference electrode RE operates as the counting electrode CE, and the counting electrode CE operates as the reference electrode RE.

Preferably, the measurements are conducted in the reverse configuration where the stimulating signal is applied on the WEn electrodes instead of the CE electrode. The reversing of the electrode configuration enables the obtaining of various result characteristics of the electrode impedance in comparison with the standard configuration. Present differences are the result of the non-linearity of the effects occurring in the sensor-biosensible layer-tested sample system. Here both the possibility to reverse the electrode polarisation (thus the direction of the electric charge movement, including ions in the solution) as well as the change in the configuration of the measuring system (the measurement method of the currents for the individual electrodes) are crucial. In particular, by this way it is possible to measure the non-linearity of the impedance characteristics which is the result of the presence of p-n junctions in the measured systems.

Preferably, the biological or chemical factors are the pathogens, especially viruses, bacteria, fungi, proteins, and fragments thereof, including enzymes, antibodies, structural proteins, antibody fragments, peptides, affibodies, nucleic acids, and nucleotide sequences, including single-stranded and double-stranded DNA, RNA, aptamers, short nucleotide sequences, fatty acids, carbohydrates, glycolipids, glycopeptides, and other organic chemical compounds such as pesticides, antibiotics, non-organic compounds, including heavy metals.

BRIEF SUMMARY OF THE DRAWINGS

Invention will be explained in more details in preferred embodiments, with references to the given figures, where.

DETAILED DESCRIPTION

Figure 1:
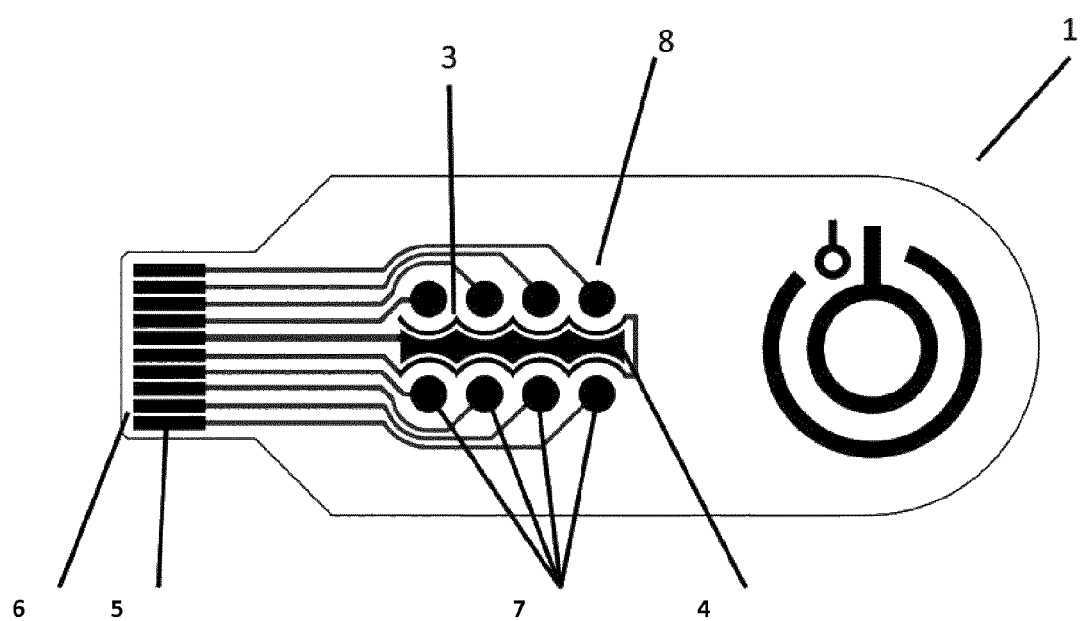
FIG. 1 presents the sensor 1 for the impedance measurements in the potentiostat system comprising the reference electrode RE 3 and the counting electrode CE 4 with the electric contacts 5 leading to the edge 6 of the sensor 1 in the form of the edge connector. Presented sensor 1 is equipped with the working electrode WEn 7 where n=8 and the reference electrode RE 3 is common for all working electrodes WEn 7 and its fragment located near the working electrode WEn 7 forms the sensing segment 8 of RE-CE-WEn type.

In the preferred embodiment the working electrodes WEn 7 are covered with the sensory material 9, thus the substance responsible for the detection of the specific biological and chemical substances and particles in the sample 2, preferably in the form of a solution or a suspension.

The working electrode RE 3 and the counting electrode CE 4 are the auxiliary electrodes which are shared during the measurement with all electrodes WEn 7 and are used to conduct the measurements of the electric quantities changing due to the chemical processes occurring in the sensory material 9 placed on the electrodes WEn 7 due to the biological or chemical factor intended for the detection in the sample 2.

The sensor edge connector 1 is mechanically and partially electrically compatible with the standard HDMI port or DisplayPort. In typical use, ports of HDMI and DisplayPort type are utilised for the transmission of the digital data and contain two rows of contacts in the casing which maintain the electric connection between the port and the inserted plug. The mechanic construction of the HDMI/DP ports and plugs prevents their reverse connection.

Yet, in the presented solution the sensor 1 is not fitted with the HDMI/DP port and any mechanic elements providing similar functionality which prevent from the reverse insertion of the sensor into the sensor slot. Thus, without any additional mechanical protection the reverse insertion of the sensor 1 in the measurement slot is possible, preventing the measurement. In such a situation an additional problem is the construction of the standard HDMI/DP port—the contacts are located in an alternating manner instead of the opposite manner, what in practice makes it impossible to use the electric contacts 5 on the edge 6 of the edge connector for an unambiguous detection of the reverse insertion of the sensor 1 in the sensor slot. This is due to the fact that by the reverse insertion the connection spots of the sensor slot and the centres of the electric contacts 5 do not overlap—the connection spot is shifted to the isolated area between the electric contacts 5. As an effect, it is possible to obtain the short-circuit of the neighbouring electric contacts 5 by the slot contact, as well as to obtain the electric connection with any of these electric contacts 5. This phenomenon is practically unpredictable and the obtained result can be completely different than the next attempts to insert the sensor 1 in the sensor slot in the reverse orientation. This is the result of the misfit of clearances between the socket housing and the edge connector and the deviation of the edge 6 of the edge connector from the right angle in relation to the socket symmetry axis.

Figure 2:
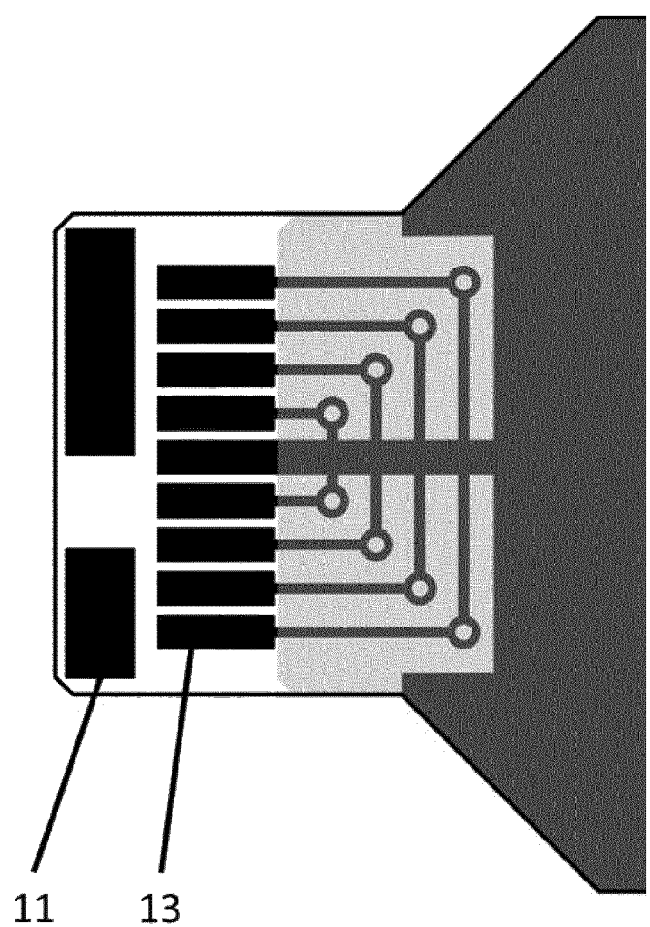
FIG. 2 presents the edge 6 of the sensor 1 in the form of the edge connector with the contact spots 11 forming the electric circuit separated from the electrodes WEn 7, RE 3 and CE 4 intended for the identification of correct sensor placement in the measurement slot and additional 13 connecting and/or non-connecting electrodes to code of the number of the working electrode WEn 7.

Unexpectedly it turned out that even though the exclusion of such a situation is not possible, it is however possible to detect correct or incorrect orientation of the sensor 1 while inserting it into the sensor slot based exclusively on the electrical measurements. It is required to design the connection spots 11 in such a manner that the part closer to the edge 6 of the sensor 1 edge connector is used as the connections spots 11 for the detection of the sensor orientation in the socket, while the other area of the edge connector maintains the electric contact of the socket connections with the electric contacts 5 connected with the individual sensor electrodes. The embodiment is presented in the FIG. 2. During insertion of the sensor 1 into the socket, the temporary connection of the contacts 1-2-3-4 and 6-7-8-9 of the connection socket through the connection spots without the connection with the contact 5 occurs. Invented method for the detection of sensor 1 orientation in relation to the slot is based fully on the electrical measurements by monitoring of the short circuits between the groups of electric connectors during insertion of the sensor 1 into the sensor socket and it does not limit functionally or impact the operation of the sensor 1 after its full insertion.

The variants of the described solution cover isolation of the connection spots 11 on upper, lower, or both sides of the edge connector in various configurations of the circuited connections of the sensor slot.

Only after detection of the correct sensor 1 orientation in the sensor slot the electric signals used for the identification of sensor 1 and required for the correct measurement are activated.

Example 1

Identification of the Sensor Type

Versatility of the sensor includes its use for the detection of various biological or chemical substances. The sensor 1 can be made in many versions which differ in types of sensory materials 9 of the working electrode WEn 7 sensitive for the specific selected pathogens or other substances. Therefore, it was necessary to enable the possibility of unambiguous identification of the type of sensor 1 located in the sensor and based on it to select the measurement conditions such as stimulation signal values and the measurement time which could vary for the individual sensor 1 types. Commonly found solutions are based on the colorimetric identification, utilisation of the codes based on the optical image analysis (e.g. bar codes, QR codes) or specialised electronic systems used for the wire or wireless identification (e.g. RFID).

The type identification of the sensor 1 is possible using the same electric contacts 5 which are used for the measurements of the working electrodes WEn 7. Coding of the sensor 1 type is conducted by the selection of the subset of N electric contacts 5 from M available, wherein N<M. Selected combination of N electric contacts 5 is further connected with the reference electrode RE 3 or the counting electrode CE 4 or the shield electrode GE 14. The sensor electric circuit detects which electric contacts 5 are connected and the electric contacts 5 connected in such a way are not used during further steps of the proper measurement.

Figure 3:
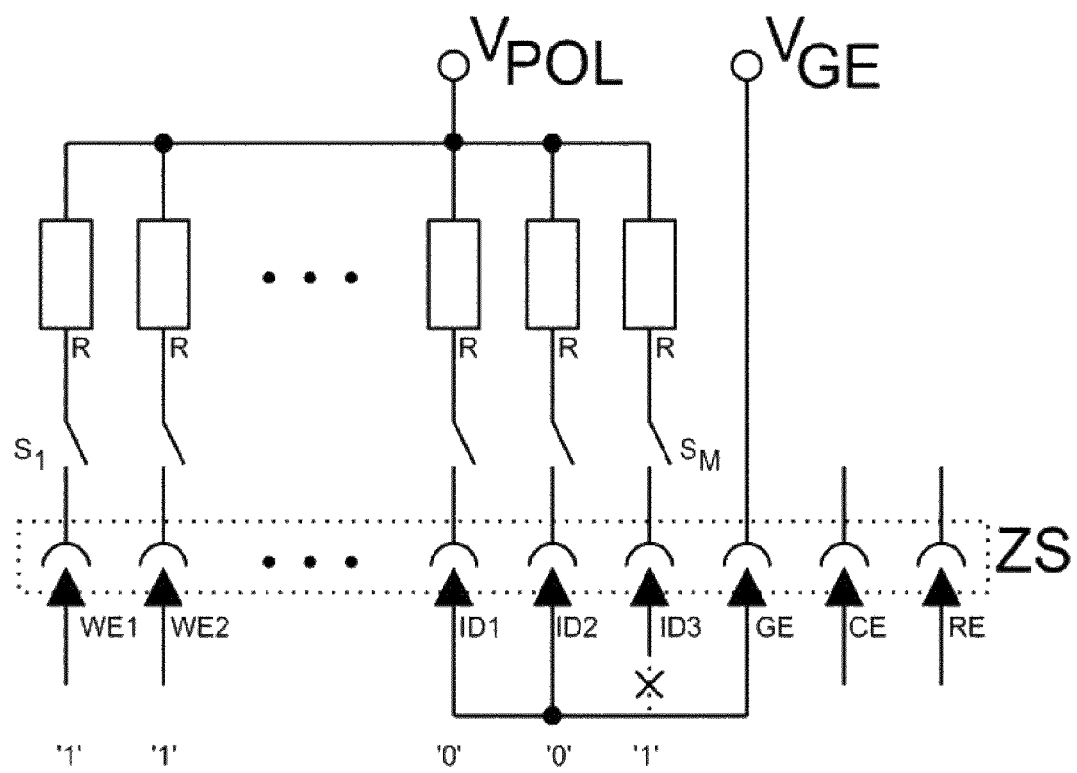
FIG. 3 presents the ideogram of the identification system of the sensor with coded number "11001". Possible number of combinations is 32 (2↑VI for M=4).

According to the FIG. 3, the electric contacts 5 number 1, 2 leading to the working electrodes WE1 and WE2 7 and the electric contact 5 number 5 were not connected electrically with any lines of the electric contacts 5 of the electrode CE 4, the electrode RE3, GE 14, thus these electrodes are used to conduct the measurement of the biological or chemical factor content. The electric contacts 5 number 3 and 4 are connected with centrally located electrode GE 14. Initial voltage polarisation VPOL in 500 mV to 5V range of all electric contact 5 in reference to GE14 or RE, CE gives the measurement result similar to VGE only for the electric contacts 5, 3, and 4, and the voltage measurement result is similar to VPOL for the electric contacts 5 number 1, 2, and 5. The code "11001" is obtained while assigning the potential similar to VGE with the "0" symbol and one similar to VPOL with the "1" symbol.

Presented solution with selected subset of the electric contacts 5 of the edge connector set in any combination connected or not connected with the electrodes GE 14, the electrodes RE 3, or the counting electrodes CE 4 enables the encoding of 2^N various combinations. For the exemplary solution, the subset of the electric contacts 5 used for the identification with N=3 of the electric contacts 5 enable the unambiguous identification of 8 different types of sensor 1. Similarly, for the N=8 it is possible to identify 256 types of the sensor 1.

The solution which enables the utilisation of all electric contacts 5 for the identification of the type of the sensor 1 provides higher number of combinations, namely 32 combinations (2^M for M=4).

Figure 4:
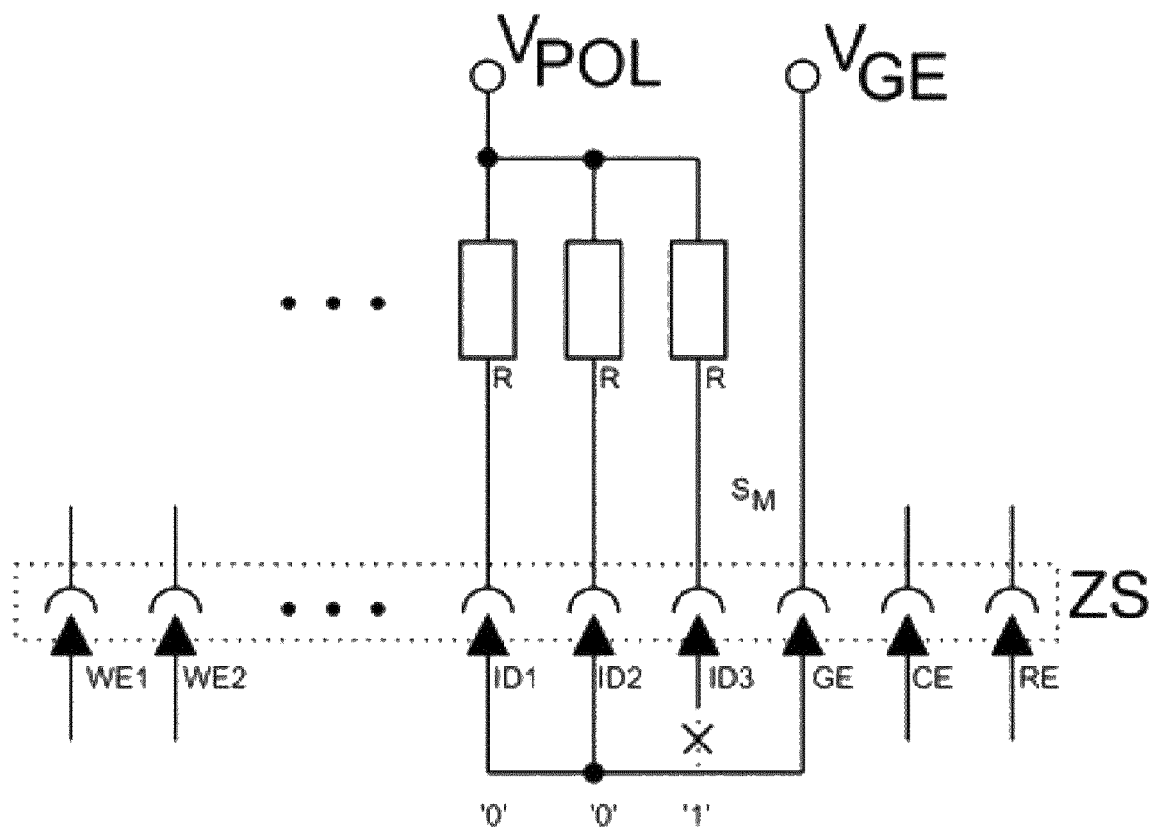
FIG. 4 presents the ideogram of the system in the simplified version; the subset of 3 electric contacts 5 is used for identification, thus the number of combinations is 2^M=8.

FIG. 4 presents layout in the simplified version; the subset contains 3 electric contacts 5, thus the number of combinations is 2^M=8.

Sensor Operation

In case of the presented solution, each individual measurement segment 8 composed of the working electrode WEn 7 and the corresponding fragment of the reference electrode RE 3 and the counting electrode CE 4 are identical, i.e. the identical distances between these elements are kept and area values are kept constant. The potential of the reference electrode RE 3 is constant in the whole system, resulting with the perfect measuring conditions for the whole system. All other electrode pairs operate identically, and the reference electrode RE 3 equalises the potential within the surroundings of other electrodes.

The working electrodes WEn 7, the reference electrodes RE3, the counting electrode CE4 are made of the material of low resistivity, e.g. copper, which is negligible comparing with the resistivity of the sample 2 or sensory material 9 reacting with the particular chemical and biological substances, e.g. pathogens being detected.

The multichannel systems exhibit a negative influence of the electric potential gradient on the results obtained from the individual channels.

In the presented solution of the multichannel sensor 1 the measuring sensors 8 are used forming the system of the working electrode WEn 7, the working electrode 3, and counting electrode 4 that each of the measuring segments 8 keeps the identical geometry, especially identical area of the individual electrodes, the distances between the electrodes, and shapes of the electrodes assigned in such a manner that the path of the RE electrode corresponds to the certain fixed potential in the distribution of the electric force field lines in the polarised sensor 1.

Unexpectedly it turned out during the conducted tests that the electrode system designed in such a manner gives both very good repeatability of results independently of the analysed WEn 7 electrode and also enables the utilisation of new impedance measurement methods.

N1 Measurement Method

Comparing with the classic impedance spectroscopy with the potentiostat system, the purpose of the reference electrode RE 7 is to measure the potential in the solution of sample 2 in the form of electrolyte in order to compensate (eliminate) the electrolyte impedance from the final result which is the impedance value within the CE-WEn electrode system instead of reaching the set potential due to the changes in the counting electrode CE 4 potential.

N2 Method

In comparison with the classic measurement method used in the impedance spectroscopy with the potentiostat, there is a change in the roles of the working electrode WEn 7 and the counting electrode CE 4 the stimulations are generated in such a system by the working electrodes WEn 7 instead of the counting electrode CE 4. The role of the working electrode RE7 similarly to the method N1 is the measurement of the potential distribution in the electrolyte. Unexpectedly, it turned out that the impedance values measured using the method N2 are different than the values obtained using the traditional method or N1 method, while cyclic switching of the operation mode for the measurement system between N1 and N2 provides additional information about the measured samples.

Both N1 and N2 methods are characterised in the lack of limitations typical for the commonly conducted impedance measurements with the potentiostat system; especially, the simultaneous execution of the measurement for all working electrodes WEn 7 is possible.

It turned out that the besides the beneficial increase in the amount of data about given sample 2 obtained while changing the N1 and N2 methods, the additional advantage is a significant reduction of the measurement time in comparison with the measurements multiplexed concerning time, based on the conduction of the separate measurements for the individual electrodes. The gain in the reduction of measurement time both using N1 and N2 method is directly proportional to the number of channels and for the 8 channels measured simultaneously is 8-times shorter than the analogous measurement with the traditional method, i.e. with the time multiplexing.

The electrolyte, unlike the situation with the classic electrochemical measurements, is just a wetting and auxiliary agent for the conduction of electricity and the geometry of electrodes eliminates the influence of the electrolyte itself on the impedance.

The construction and mutual arrangement of the electrodes also enables the usage of the reverse detection mode. In the classic system the stimulation occurs at the counting electrode CE 4 and the signal is registered with the working electrode WEn 7. In case of the given solution, the measurement can be conducted in such a way that the stimulation at the working electrode WEn 7 and the counting electrode CE 4 is used as a reference for the whole measurement system. Reversing of the ion current direction through the electrolyte gives the result which differs in some frequency range from the result obtained using a traditional method, what improves the device sensitivity and increases its capabilities concerning the automatic malfunction detection for the sensor 1 or the individual electrodes.

Example 2

Analysis of the Lactose-Electrode Interactions

Figure 5:
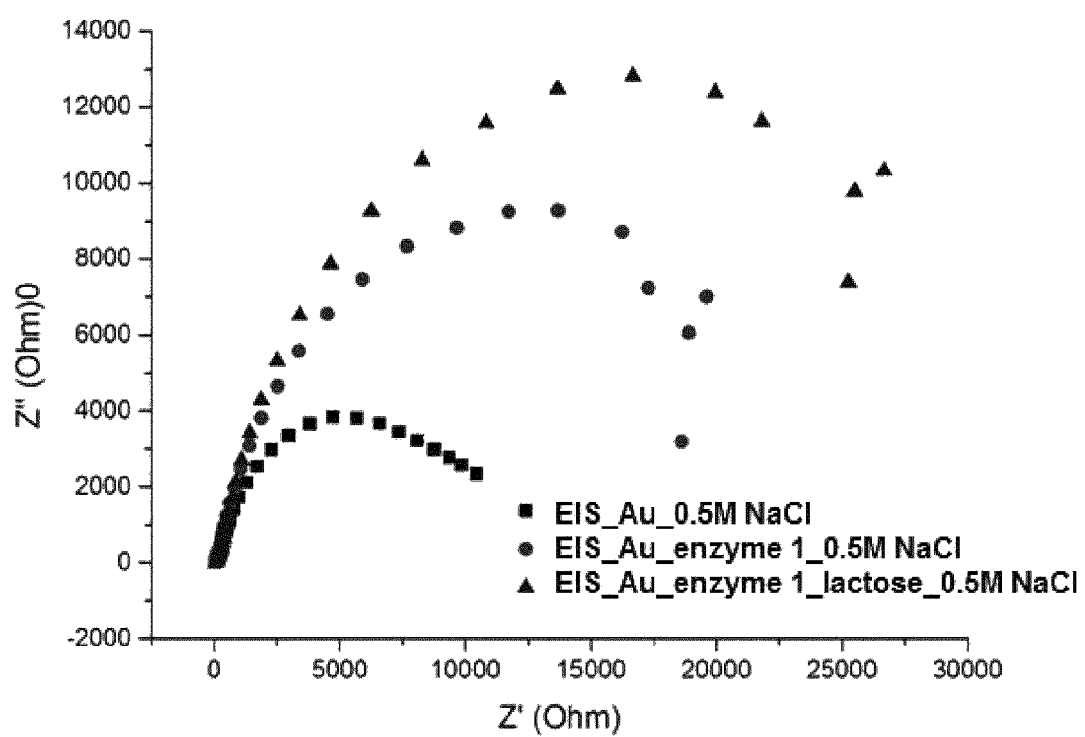
FIG. 5 The measurement of the sensor interaction with the positive sample, the lactose product.

The surface of the working electrode WEn 7 is modified with the beta-galactosidase enzyme. Subsequently, the working electrode WEn 7 is zeroed with the buffer (prepared for work, thus moistened with the zeroing solution used for the electrode activation) and subsequently the sample 2 is applied as the lactose-containing solution. FIG. 5 shows the distinct change in the impedance in case of the lactose presence.

Figure 6:
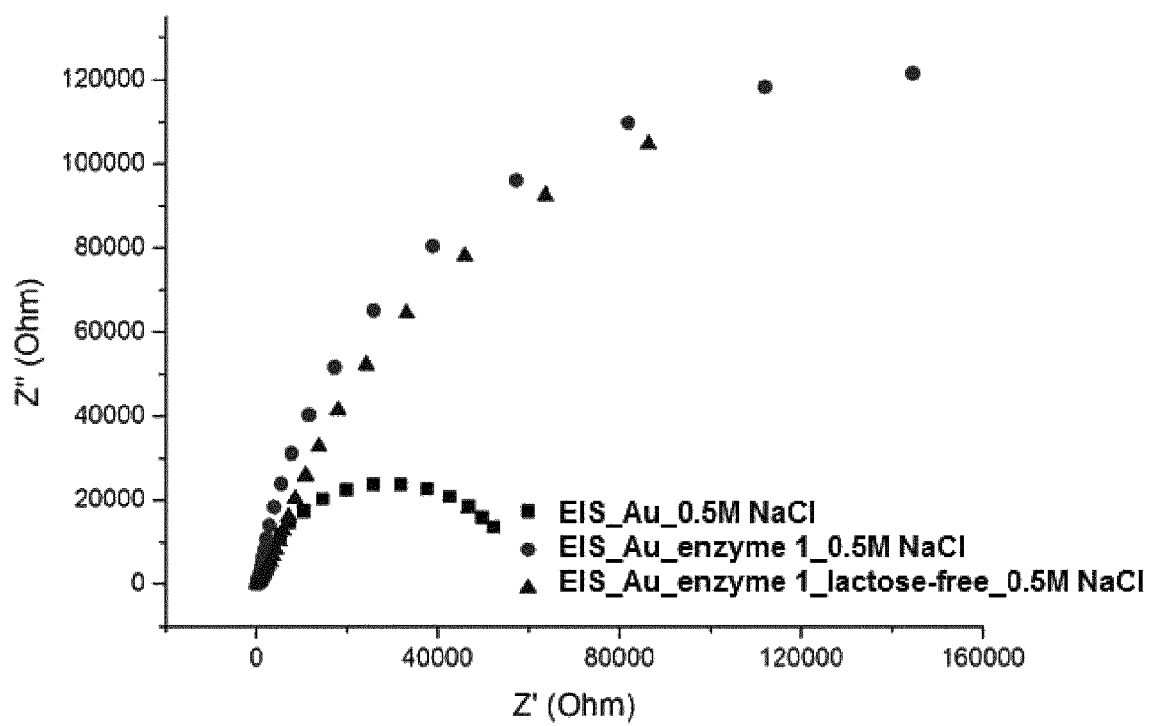
FIG. 6 The measurement of the sensor interaction with the negative sample, the lactose-free product.

The lactose-free sample was used as the control experiment. As shown in FIG. 6, the sensor 1 does not exhibit changes during presence of the control sample.

Example 3

Analysis of the DNA Interactions on the Electrodes

The working electrodes WEn 7 number 1 to 8 are washed with $H_2SO_4$ before the measurement. First, the measurement with clean working electrodes WEn 7 is conducted and subsequently the sensory material 9 is prepared on them. The sensory material 9 is prepared by:

Deposition of the modifying SH-DNA form (ssDNA) and incubation in the room temperature for 2-24 h.

Subsequently, application of 10 µl of MCH solution is conducted (complementary DNA, CssDNA) and wash with PBS buffer, pH 7.4 is performed to remove unbound molecules. The sensor 1 prepared in such a manner with the sensory material 9 enable conduction of the measurements, e.g. with the electrochemical impedance spectroscopy which show the interaction of modifying SH-DNA (attached to the electrode surface) with the complementary DNA present in the measured sample.

Figure 7:
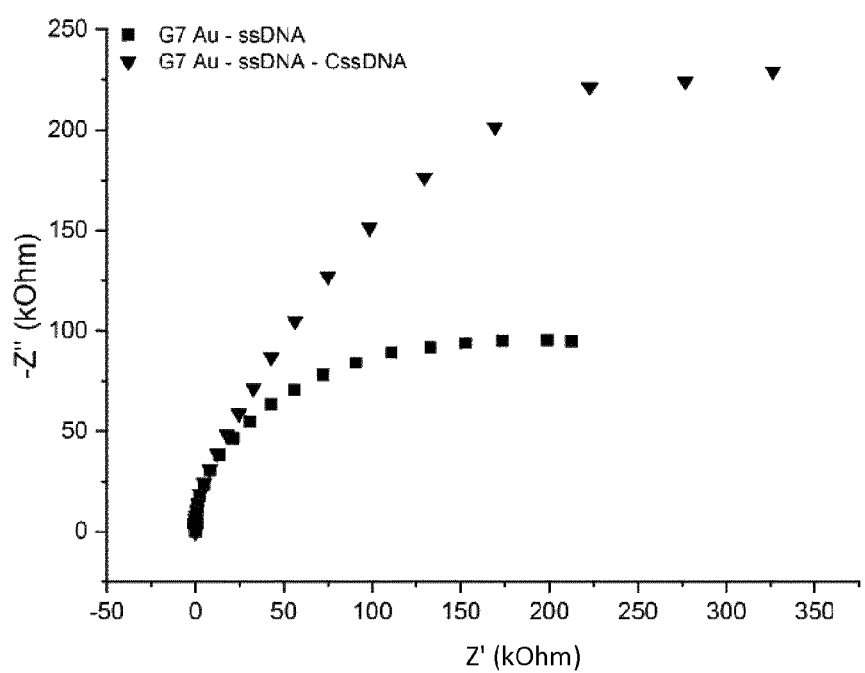
FIG. 7 The interaction of the ssDNA-modified sensor with a complementary sequence.
Figure 8:
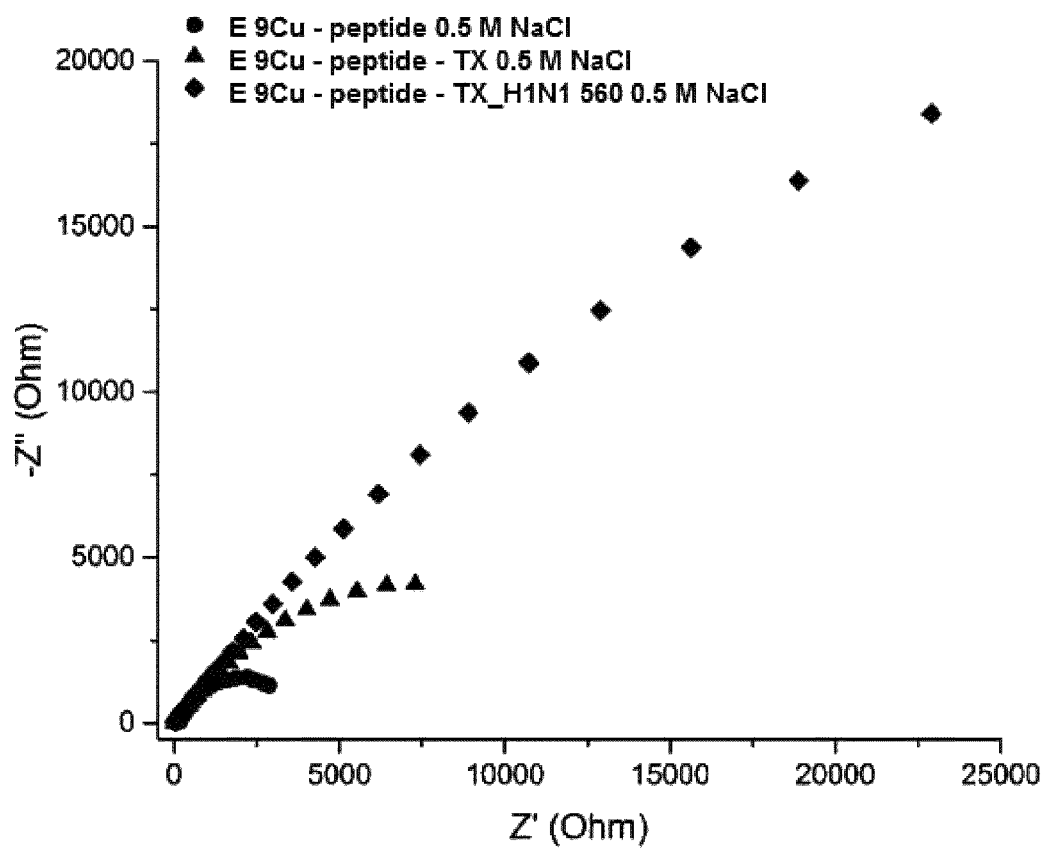
FIG. 8 The result of the Electrochemical Impedance Spectroscopy measurement for the copper electrode covered with the biological layer treated successively with 0.5 M NaCl, artificial saliva with Triton X buffer (1%), H1N1 virus in Triton X buffer with 0.5 M NaCl additive.
Figure 9:
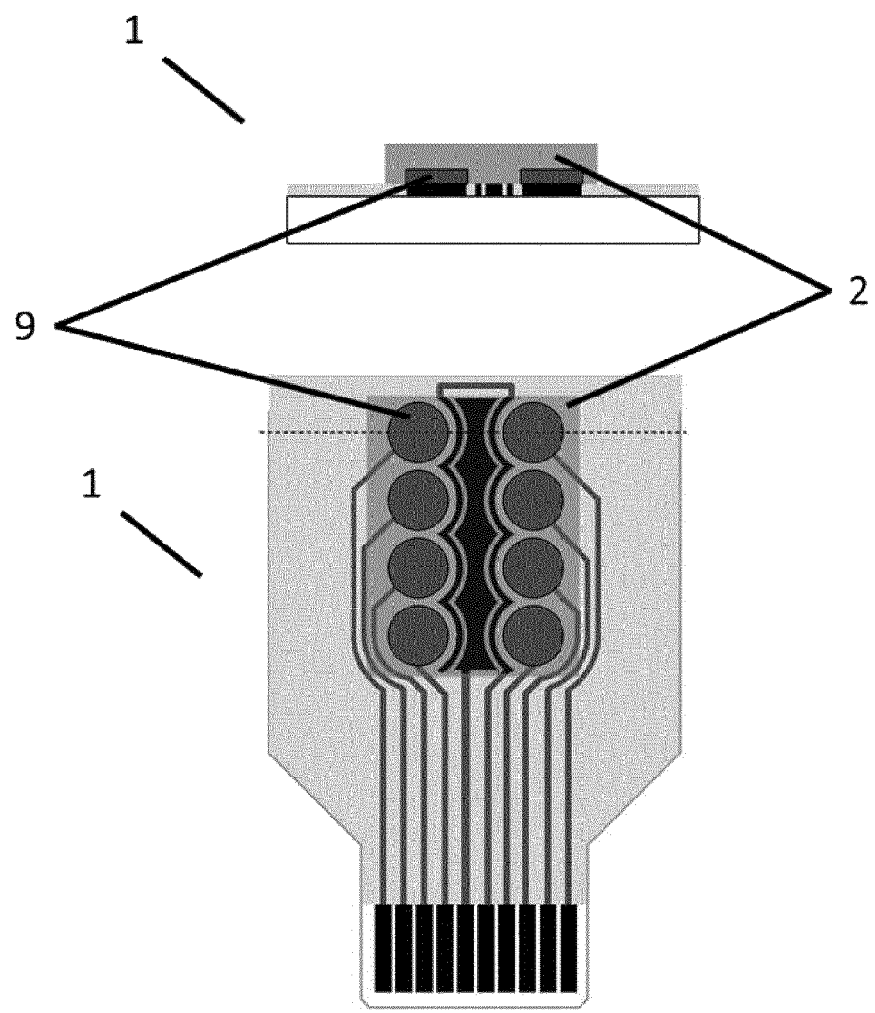
FIG. 9 Top view and cross section of the sensor 1 covered with the sensory material 9 (biological layer) and the applied sample 2 of the biological or synthetic factor.

The results are shown in the graph (FIG. 7) where the increase in the impedance is caused by the interaction of the complementary DNA with the modifying DNA.

Example 4

Analysis of the Copper Surface Sensor Interactions Virus H1N1 560 modification of the sensor surface with the biological layer (with the anti-M1 antibody)

so called "zeroing" of the sensor modified with the antibody step one of the proper measurement of the sensor biological activity as the result of which the dried peptide layer is prepared for the tests, analysis of the sensor interactions with the negative sample in form of the artificial saliva with an additive of 1% Triton X the analysis of the interactions of sensor with the sample containing H1N1 virus The results are shown in the FIG. 8

Results: the sensor made on the copper basis modified with the antibody:

shows a slight change in the impedance during interaction with the negative sample, artificial saliva with the addition of 1% Triton X;

shows a distinct change (increase) in the impedance during interaction of the peptide with the virus-containing sample.

The invention claimed is:

1. A sensor for impedance measurements of a biological or chemical factor sample in a potentiostat system, comprising a reference electrode RE and a counting electrode CE with electric contacts leading to an edge of the sensor in the form of an edge connector, the sensor comprising n working electrodes WEn, wherein n is in a range of 2 to 256;

the reference electrode RE is common for all working electrodes WEn and a fragment thereof present by working electrode WEn forms a measuring segment RE-CE-WEn; and the edge connector comprises an HDMI port or a DisplayPort.

2. The sensor according to claim 1, wherein at least one working electrode WEn is covered on an outer surface with a layer of sensory material, wherein the sensory material reacts only with one type of biological or chemical factor in a sample.

3. The sensor according to claim 2, wherein at least two working electrodes WEn are covered on an outer surface with various sensory materials.

4. The sensor according to claim 2, wherein the sensory material is a biological or synthetic type, and are selective antibodies, antibody fragments, peptides, nucleic acid sequences for detection of the biological or chemical factor in the sample.

5. The sensor according to claim 1, wherein the working electrodes WEn comprise uniform circles and are located symmetrically to the counting electrode CE, wherein edges of the counting electrode CE are concentric with the circles, the reference electrode RE is located between the counting electrode CE and the working electrodes WEn, and the reference electrode RE has a same shape as the counting electrode CE.

6. The sensor according to claim 1, further comprising additional connecting and/or non-connecting electrodes to code a number of the working electrode WEn.

7. The sensor according to claim 1, wherein an arrangement of the working electrodes WEn, the counting electrode CE, and the reference electrode RE constitutes a repeating measurement segments of the identical shape and in each measurement segments the distances between the working electrode WEn, the counting electrode CE, and the reference electrode RE are the same, and in addition an area of the working electrode WEn, the counting electrode CE fragment, and the reference electrode RE fragment are respectively the same in each segment.

8. The sensor according to claim 7, wherein the arrangement and shape of the working electrodes WEn, the reference electrode RE, and the counting electrode CE have the symmetry axis.

9. The sensor according to claim 1, wherein the edge connector further comprises contact spots which constitute an electric circuit independent of the WEn electrodes, the reference electrode RE, and the counting electrode CE for the identification of a correct location of the sensor in a measurement slot by connection of measurement slot contacts while placing the sensor in the slot.

10. A detection method of a biological or chemical factor in a sample having a biological or chemical factor in a form of a suspension or solution placed in a device comprising the steps of:

placing the sample in a device comprising the sensor according to claim 1, covering all the working electrodes WEn, the counting electrode CE, and the reference electrode RE with the sample in the form of suspension or solution, subsequently conducting 2 to 256 sample impedance measurements simultaneously using an impedance spectroscopy technique or voltammetry, and determining, based on results of the measurements, a presence of the biological or chemical factor in the sample.

11. The method according to the claim 10 wherein the measurements are conducted in a reverse configuration where the reference electrode RE operates as the counting electrode CE and the counting electrode CE operates as the reference electrode RE.

12. The method according to the claim 10, wherein the measurements are conducted in a reverse configuration where the working electrode WEn operates as the counting electrode CE and the counting electrode CE operates as the working electrode WEn.

13. The method according to claim 10, wherein the biological or chemical factor is at least one of pathogens, viruses, bacteria, fungi, proteins, and fragments thereof, enzymes, antibodies, structural proteins, antibody fragments, peptides, affibodies, nucleic acids, and nucleotide sequences, single-stranded and double-stranded DNA, RNA, aptamers, short nucleotide sequences, fatty acids, carbohydrates, glycolipids, glycopeptides, organic chemical compounds, pesticides, antibiotics, non-organic compounds, and heavy metals.

* * * * *